United States Patent [19]

Usher et al.

[11] Patent Number: 5,637,683
[45] Date of Patent: Jun. 10, 1997

[54] NUCLEIC ACID ANALOG WITH AMIDE LINKAGE AND METHOD OF MAKING THAT ANALOG

[75] Inventors: David A. Usher; Mark F. Harris, both of Ithaca; Clarence J. Wang, Suffern, all of N.Y.

[73] Assignee: Cornell Research Foundation, Inc., Ithaca, N.Y.

[21] Appl. No.: 502,196

[22] Filed: Jul. 13, 1995

[51] Int. Cl.⁶ .............................. C07H 19/00; C12Q 1/68; C12N 15/00
[52] U.S. Cl. ............... 536/22.1; 536/23.1; 536/25.3; 536/25.31; 536/25.32; 435/6; 935/76; 935/77; 935/78
[58] Field of Search .................. 536/22.1, 23.1, 536/25.3, 25.32, 25.31; 935/76, 77, 78; 435/6

[56] References Cited

PUBLICATIONS

Eghol m, et al., "Peptide Nucleic Acids (PNA), Oligonucleotide Analogues with an Achiral Peptide Backbone," *J. Am. Chem. Soc.*, 114(5):1895–97 (1992).

Chur, et al., "Synthesis of a Carboxamide Linked T*T Dimer and its Incorporation in Oligonucleotides," *Nucleic Acids Research*, 21(22):5179–83 (1993).

Lebreton, et al., "Synthesis of Thymidine Dimer Derivatives Containing an Amide Linkage and Their Incorporation Into Oligodeoxyribonucleotides," *Tetrahedron Letters*, 34(40):6383–86 (1993).

De Mesmaeker, et al., "Novel Backbone Replacements for Oligonucleotides," in *Carbohydrate Modifications in Antisense Research*, 24–39, Yogesh Sanghui and P. Dan Cook, Eds. (1994).

De Mesmaeker, et al., "Amides as a New Type of Backbone Modification in Oligonucleotides," *Angew. Chem. Int. Ed. Engl.*, 33(2):226–29 (1994).

Verheggen et al. "Synthesis and Antiherpes Virus Activity of 1,5–Anhydrohexitol Nucleosides" J. Med. Chem., vol. 36, pp. 2033–2040 1993.

Jois et al. "Synthesis and Antiviral Evaluation of Some Novel [1,2,4]Triazolo[4,3–b][1,2,4]triazole Nucleoside Analogs" J. Heterocyclic Chem., vol. 30, pp. 1289–1292 1993.

Neidlein et al. "Syntheses and Investigations of [Oxazolo[2,3–a]isoindol–9b(2H)–yl]phosphonates and phosphinates: a New Class of Heterocycles" Helv. Chim. Acta, vol. 76, pp. 2407–2417 1993.

*Primary Examiner*—George C. Elliott
*Assistant Examiner*—Jezia Riley
*Attorney, Agent, or Firm*—Nixon, Hargrave, Devans & Doyle

[57] ABSTRACT

The present invention relates to a nucleic acid analog having the formula:

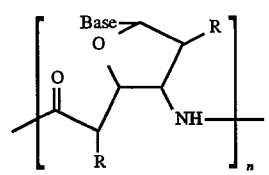

where

R is a compound selected from a group consisting of hydrogen, a hydroxyl group, a hydrophilic group or a hydrophobic group, n is greater than or equal to 2, and Base is uracil, adenine, guanine, cytosine, thymine or hypoxanthine, with Bases in the analog being the same or different. Further, the present invention relates to a processes for making and using the analog.

32 Claims, No Drawings

NUCLEIC ACID ANALOG WITH AMIDE LINKAGE AND METHOD OF MAKING THAT ANALOG

FIELD OF INVENTION

The present invention relates to a nucleic acid analog having an amide linkage and to processes for making and using the analog.

BACKGROUND OF THE INVENTION

In the past several years, much attention has been given to the development of "antisense reagents" for possible therapeutic use. This is primarily due to the discovery that the root cause of many observed pathologies is a specific genetic sequence and the protein that it encodes. Such a sequence may be an abnormal segment in the nature genome of a diseased organism, or may be introduced into an organism by some foreign infectious agent. "Antisense" (or complementary) therapy involves specifically targeting and selectively binding to this specific genetic sequence.

More specifically, in the antisense approach, synthetic oligonucleotides are constructed with specific sequences to bind to mRNAs encoded for undesired proteins. Once mRNA is bound to the antisense oligomer, translation into the corresponding protein is blocked. Thus, by controlling gene expression, antisense therapy promises a class of antiviral drugs that offer a new strategy to treat human diseases.

In recent years, research in the area of antisense has experienced a dramatic surge in the wake of several concurrent advances in cell and molecular biology. Interest in the concept of antisense control was revived following the identification of naturally occurring antisense mechanisms in the genetic processes of prokaryotes. The role of native antisense RNA transcripts in regulating DNA replication in the E. coli plasmid ColE1 was demonstrated (Itoh, et al., J. Proc. Nail Acad Sci. USA 1980, 77, 2450). Subsequent investigators have implicated antisense RNA in the control of gene transcription, mRNA translation, and phage development in a variety of bacteria, phage, and plasmid systems (Green, et al., Annu. Rev. Biochem. 55: 569–597 (1986); Simons, Antisense Nucleic Acids and Proteins, Fundamentals and Applications; Mol, et al.; Marcel Dekker, Inc., (1991). There is evidence that such mechanisms may be operative in eukaryotic systems as well (Knochbin, S.; et al., EMBO J, 8: 4107. (1989)).

Another development which spurred interest in antisense research in recent years was the elucidation of the viral origin of AIDS and other diseases, including certain types of cancer. The discovery that the activity of a few key genes could have such devastating consequences brought on the realization that the search for new therapeutics must be broadened and intensified. More importantly, the recognition that these disease mechanisms operate by exploiting normal cellular genetic processes clarified the need for development of drugs of much greater specificity.

Finally, the last decade has also witnessed explosive progress in methods of chemical synthesis and sequencing of oligonucleotides (Caruthers, Science, 230: 281 (1985); Beaucage, et al. Tetrahedron, 48: 2223 (1992)). These advances in nucleic acid chemistry have increased the availability of a broad spectrum of oligonucleotide research materials. As a consequence of these recent developments, progress in the antisense field has quickly reached a point where the wide range of potential antisense applications is evident (Zon, G. Pharm. Res., 5: 539–549 (1988); Englisch, et al.; Angew, Chem. Int. Ed. Eng., 30: 613–629 (1991); Mol, et al.; Antisense Nucleic Acids and Proteins, Fundamentals and Applications; Marcel Dekker, Inc.; (1991)).

As a first step in the development of nucleic acid based pharmaceuticals, scientists have examined the potential of natural oligonucleotides as antisense therapeutics. Recent reports have concentrated on the HIV system (Goodchild, et al., Proc. Natl. Acad Sci. U.S.A., 85: 5507–11 (1988)), showing that in the presence of oligodeoxyribonucleotides complementary to viral RNA, replication of HIV is inhibited. Even while illustrating the therapeutic potential of antisense, this work also highlights two important obstacles: delivery and stability of the antisense compounds.

An oligonucleotide is a highly polar species by virtue of the negatively charged phosphodiester groups linking each nucleotide unit. Cellular uptake of mononucleotides has been shown to be nearly non-existent (Montgomery, et al., J. Med Chem., 24: 184–189 (1981)), while on the other hand, large DNA molecules were observed to enter cells (probably by pinocytosis) (Ledous, Prog. Nucl. Acid Res. Molec. Biol., 4: 23 1–267 (1965)). It is not yet clear where oligonucleotides fall in this range of behavior. It was initially assumed that the anionic character of natural oligonucleotides would render their transfer across the hydrophobic cell membrane a difficult process. However, there is now evidence that such transfer occurs as an active process modulated by specific membrane recepfors (Loke, et al., Proc. Nail Acad Sci. USA 1989, 86, 3474–3478; Yakubov, et al., Proc. Natl Acad Sci. USA 1989, 86, 6454–6458). In the HIV work, as well as in many other studies of antisense activity in oocytes and embryos, the problem of oligonucleotide delivery was circumvented by direct administration of the antisense oligonucleotides via microinjection of individual cells.

The second challenge to antisense therapy arises from the observation that the inhibitory effect of antisense oligodeoxynucleotides is quickly lost due to their rapid degradation by cellular nucleases, the native enzymes responsible for hydrolysis of nucleic acids in the cell. Both of these obstacles must be addressed if the antisense strategy is to be successfully developed as a therapeutic approach.

Approaching from the perspective of organic chemistry, researchers have investigated a variety of synthetic oligonucleotide analogs designed specifically to counter the problems of hydrolytic instability and low membrane permeability presented by natural nucleic acids. These chemical approaches range from use of nucleotide stereoisomers to modification or replacement of the natural phosphodiester linking group.

The complete replacement of the phosphodiester linkage with some other connecting functionability is the most radical approach to synthesizing oligonucleotides. The low energy conformations of a new linking group must accommodate oligonucleotide geometry in which the heterocyclic bases are in the proper orientation to maintain base-pairing with a complementary strand. As might be expected, this approach has met with widely varying results.

Earlier results in this area came from the work of Halford and Jones in 1968 towards the synthesis of polymers of a thymidine analog, linked by a 3'(O)→5'(O) carboxymethyl functionality. These researchers were perhaps the first to point out the theoretical advantage conferred by non-ionic linkages on the ability of an oligonucleotide to penetrate a cell membrane. A carboxymethyl-linked dimer of thymidine and uridine exhibited a larger hypochromic effect than either dithymidine phosphate or polyuridylic acid. This was attributed to the fact that the carboxymethyl group has one more atom than the phosphodiester linkage and therefore greater flexibility, allowing increased interaction between the nucleobases. Random length polymers of carboxymethyl-linked thymidine also showed hypochromic behavior in solution with polyadenylic acid, but not with polyuridylic acid or random sequence DNA. The success of this work led the researchers to hypothesize about the use of such analogs in modulating mRNA function in biological systems.

Workers from the Jones laboratory also investigated this novel linkage in the 5'(O)→3'(O) reverse orientation (Bleaney, et al.; Nucl. Acids Res., 2: 690–706 (1975)). Polydeoxynucleotide analogs containing thymine, adenine, or cytosine were shown to bind their respective complementary polynucleotides, poly(A), poly(U), and poly(I). However, testing for biological activity of these compounds was hampered by their low solubility, and hydrolytic instability at pH values above 5.0.

The Birmingham group subsequently pursued the 3'(O)→5'(C) acetamidate-linked analogs in an attempt to improve the solubility and stability of the oligonucleotides (Gait, J. Chem. Soc., Perkin I, 1389–1394 (1979)). Unfortunately, investigation of the interaction of poly(dC) and poly(T) acetamidate-linked analogs with poly(I) and poly(A), respectively, revealed no evidence of hybridization or base-stacking, in contrast with the carboxymethyl-linked polymers. The reduced flexibility of the amide group compared to the ester group apparently destabilizes the duplex-forming geometry for the acetamidate polymer. Interestingly, this conformational restriction was not evident in a model of an acetamidate-linked thymidine dimer, but became apparent in a model containing three such linkages. The 3'(O)→5'(N) carbamate linkage was also introduced by the Jones group in 1974 (Gait, et al.; J. Chem. Soc., Perkin I, 1684–1986 (1974)). Dimers, and later, trimers prepared by Mungall and Kaiser (Mungall, et al. J. Org. Chem, 42: 703–706 (1977)), were reported to have excellent stability to chemical and enzymatic hydrolysis. The hybridization properties of carbamate-linked oligonucelotide analogs were investigated in 1987 by Weith and coworkers (Coull, et al., Tetrahedron Lett., 28: 745–748 (1987)). A hexamer incorporating the carbamate linkage was prepared from thymidine by cycles of 3-O-carbonylimidazolide formation and condensation with free 5'-amino-5'-deoxythymidine. This compound showed no ability to hybridize the complementary poly(A) or poly(dA). In comparison, the deoxycytidine analog, prepared by block synthesis of dimeric 5'-amino-2',5'-dideoxycytidine, exhibited strong binding to both poly (dG) and poly (G) (Stirchak, et al.; J. Org. Chem., 52: 4202–4206 (1987)).

Matteuci has described the synthesis of an oligonucleotide containing the "simplest and smallest isostere" of the phosphodiester group, a formacetal linkage. (Matteuci, Tetrahedron Lett., 31: 2385–2388 (1990)). This group was incorporated into a thymidine trimer used as the 3'-terminus for solid-support-synthesis of a 15-mer of thymidine and deoxycytidine of which only the last two linkages are modified. The melting profile of this oligonucleotide analog with its RNA complement was measured. The $T_m$ (a measure of the strength of the base-pairing interaction) was slightly lower than that of the unmodified oligonucleotide, but higher than that of an analog with two methoxyethylphosphoramidate linkages at the 3'-terminus. Since the analog linkage was studied only in the terminal positions of a chimeric structure containing a majority of normal linkages, little information was revealed about the inherent ability of this group to support duplex geometry.

The Nielsen group has reported the preparation of an achiral peptide nucleic acid (PNA) backbone consisting of (2-aminoethyl)glycine units with thymine bases attached via methylenecarbonyl linkers (Nielsen, Science, 254: 1497–1500 (1991); Egholm, et al.; J. Am. Chem. Soc., 114: 1895–1897 (1992)). This structure was designed by replacement of the deoxyribose phosphate backbone in a computer model of B-DNA. The binding affinity of PNA for normal DNA was found to be so strong that a PNA thymidine decamer displaced the $dT_{10}$ strand of a $dA_{10}.dT_{10}$ duplex to give a hybrid with an increased $T_m$. The researchers attribute the surprising strength of this binding to the lack of electrostatic repulsion between the duplex strands, and the constrained flexibility of the polyamide backbone. Mixed sequence PNA oligomers are currently under investigation.

To date, most of the replacements of the phosphodiester linkage that lead to an increased resistance towards nucleases are also connected with a decrease in the affinity for a complementary RNA strand. (Cohen, et al., Oligodeoxynucleotides: Antisense Inhibitors of Gene Expression, CRC Press, Inc. 1989). Therefore, further investigation is needed to study replacement backbones which are both able to strongly bind to a complementary sequence of DNA or RNA, and to offer increased resistance toward nucleases. Replacement of the natural phosphodiester linkage by an amide linkage was undertaken in an effort to overcome these problems.

A study of amide based linkages replacing the phosphodiester based backbones was described in Alain De Mesmaeker, et al., "Novel Backbone Replacements for Oligonucleotides", Carbohydrate Modifications in Antisense Research, Sanghvi & Cook, Eds. 1994. Thymidine dimers having the following formulas were synthesized:

| | W | X | Y | Z |
|---|---|---|---|---|
| 1 | NH | CO | $CH_2$ | $CH_2$ |
| 2 | $CH_2$ | $CH_2$ | NH | CO |
| 3 | $CH_2$ | CO | NH | $CH_2$ |
| 4 | $CH_2$ | NH | CO | $CH_2$ |
| 5 | CO | NH | $CH_2$ | $CH_2$ |

These dimers with amide based linkages were incorporated into oligonucleotides where the other linkages between the nucleosides were normal phosphodiester bonds. The affinity of the oligonucleotide to its complementary RNA strand was studied. Affinity of the corresponding oligonucleotide for an RNA target was increased. Further, the oligonucleotide's resistance towards nucleases was also increased. However, it was determined that desired thermal stability would be improved by adjusting the distance between the sugars, as well as by having a more rigid backbone.

In Jacques Lebreton, et al., "Synthesis of Thymidine Dimer Derivatives Containing an Amide Linkage and their Incorporation into Oligodeoxyribonucleotides," Tetrahedron Letters, 34 (40): 6383–6386 (1993), the synthesis of thymidine dimers with an amide group backbone is disclosed. The amide backbone is of the structure 3'-NR—CO—CH$_2$-5' (R=H, Me, N-Pr). On binding with complementary RNA, destabilization occurred.

In Alain De Mesmaeker, et al., "Amides as a New Type of Backbone Modification in Oligonucleotides," Angew. Chem. Int. Ed. Engl., 33 (2): 226–229 (1994), an amide function backbone in thymidine dimers of the type CH$_2$—NH—CO—CH$_2$ (and isomers thereof) was disclosed as shown below:

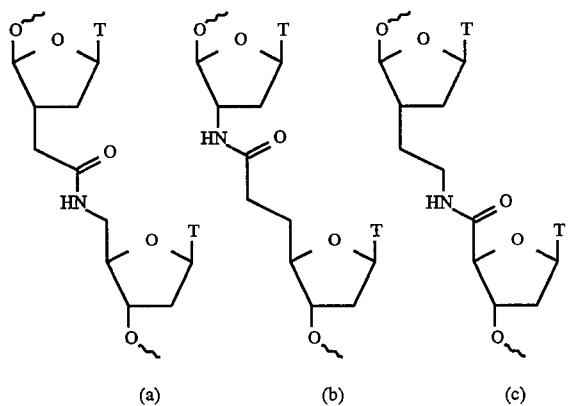

Increased affinity to the complementary DNA strand and RNA target and increased stability towards nucleases was discovered for the structure shown in (a) when a single amide modified backbone was incorporated in the middle of the oligonucleotide. Results for structures (b) and (c) were less satisfactory.

In Anette Chur, et al, "Synthesis of a Carboxamide Linked T*T Dimer and Its Incorporation in Oligonucleotides," Nucleic Acids Research, 21 (22): 5179–5183 (1993), a dimer containing a five atom carboxamide linker (3'-OCH$_2$CH$_2$NHC(O)-4') was disclosed. The incorporation of this dimer in oligonucleotide sequences showed moderately lowered T$_m$ values when hybridized with a complementary DNA relative to the unmodified DNA complex.

Although the amide based linkages investigated above showed increased affinity to complementary sequences and increased stability toward nucleases, the backbones investigated have four or five bond linkages, and, therefore, are relatively flexible. A flexible backbone has inherent disadvantages. Development of a more rigid backbone is desirable to provide greater binding strength during hybridization of the oligonucleotides to the complementary DNA or RNA sequence. Further, a more rigid backbone is likely to be less tolerant to mismatches to non-complementary DNA or RNA. In addition, four and five bond linkages are more difficult to synthesize than a shorter backbone. The present invention is directed to overcoming these difficulties.

SUMMARY OF THE INVENTION

The present invention relates to a nucleic acid analog having the formula:

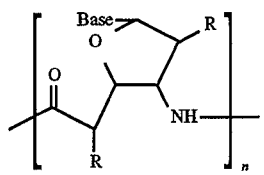

where

R is a compound selected from a group consisting of hydrogen, a hydroxyl group, a hydrophilic group, or a hydrophobic group, n is greater than or equal to 2, and Base is uracil, adenine, guanine, cytosine, thymine or hypoxanthine, with Bases in the analog being the same or different.

Another aspect of the invention is a nucleoside analog having the formula:

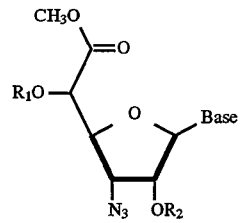

where

R$_1$ and R$_2$ are protecting groups,

Base is thymine, adenine, guanine, cytosine, uracil or hypoxanthine.

Another aspect of the present invention involves an antisense treatment method which involves introducing into a cell an analog having the formula:

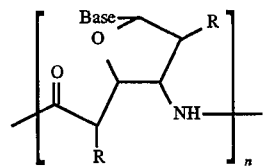

where

R is a hydrogen, a hydroxyl group, a hydrophilic group or a hydrophobic group, n is greater than or equal to 2, and Base is uracil, adenine, guanine, cytosine, thymine or hypoxanthine, with Bases in said analog being the same or different.

The analog is contacted with any mRNA, having a nucleic acid sequence complementary to that of the analog which is present in the cell, under conditions effective to hybridize the analog to the mRNA. As a result, translation of the mRNA into its encoded protein is blocked.

Yet another aspect of the present invention relates to a method of detecting the presence of target nucleic acids in a test sample using an analog with a label and having the formula:

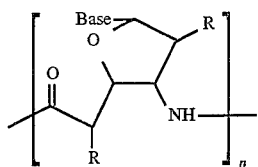

where

R is a hydrogen, a hydroxyl group, a hydrophilic group or a hydrophobic group, n is greater than or equal to 2, and Base is uracil, adenine, guanine, cytosine, thymine or hypoxanthine, with Bases in said analog being the same or different.

The test sample, potentially containing a target DNA molecule or a target RNA molecule having a nucleic acid sequence complementary to that of the analog, is contacted with the analog under conditions effective to hybridize the analog to any of the target DNA molecule or the target RNA molecule present in the sample. Thus, any target DNA molecule or target RNA molecule present in the sample is detected.

Yet another aspect of the present invention is a process of producing a nucleic acid analog which comprises providing an amine having the formula:

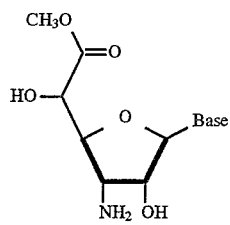

where

Base is uracil, adenine, guanine, cytosine, thymine or hypoxanthine, providing a pentafluorophenyl ester having the formula:

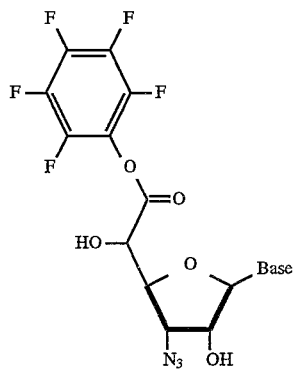

where

Base is uracil, adenine, guanine, cytosine, thymine, or hypoxanthine; and reacting the amine and the pentafluorophenyl ester under conditions effective to produce a nucleic acid analog having the formula:

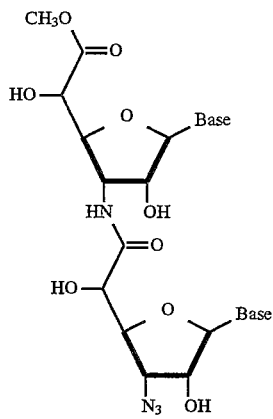

Yet another aspect of the present invention relates to a process for making the nucleic acid analog having the formula:

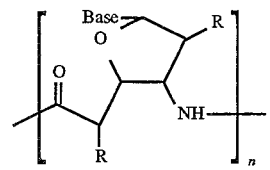

where

R is hydrogen, a hydroxyl group, a hydrophilic group or a hydrophobic group n is greater than or equal to 2; and Base is uracil, adenine, guanine, cytosine, thymine or hypoxanthine, where the processes comprises providing an amine intermediate having the formula:

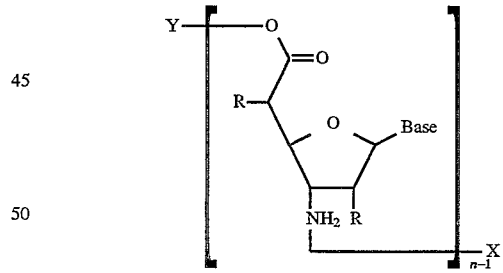

where

R is hydrogen, a hydroxyl group, a hydrophilic group or a hydrophobic group,

X is a protecting group, and

Y is a solid support.

The amine intermediate is reacted with an acid under conditions effective to remove the protecting group and to make the amine intermediate nucleophilic. The amine intermediate then is reacted with additional amines, each having the formula:

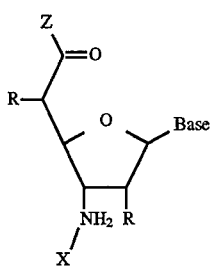

where
Z is a leaving group
X is a protecting group
R is hydrogen, a hydroxyl group, a hydrophilic group or a hydrophobic group,
under conditions effective to produce the nucleic acid analog.

DETAILED DESCRIPTION OF THE INVENTION

The present invention relates to a nucleic acid analog having the formula:

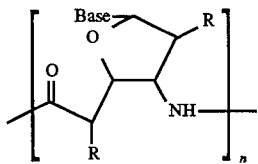

where
R is a compound selected from a group consisting of hydrogen, a hydroxyl group, a hydrophilic group or a hydrophobic group,
n is greater than or equal to 2, and
Base is uracil, adenine, guanine, cytosine, thymine, or hypoxanthine, with Bases in said analog being the same or different.

The definitive property of an antisense reagent is the ability to form a stable base-paired complex with a target nucleic acid sequence. A highly conformationally-mobile oligonucleotide analog would have the greatest likelihood of forming a double-stranded complex with a natural polynucleotide. However, the binding strength of such a complex would actually be reduced for an overly flexible molecule, due to the high entropic cost of freezing the duplex geometry out of a large range of possible conformations (Breslow, Ann. N.Y. Acad Sci., 471: 60–69, 1985), which is hereby incorporated by reference. It is more logical to design the analog structure so that its conformational freedom is inherently restricted, but where the most favored geometry is precisely that required for duplex formation. Clearly, the design process should make use of available modeling tools, in order to identify structural incompatibilities prior to commencing synthetic work.

Further, the analog must be stable to chemical hydrolysis under the conditions of oligonucleotide synthesis. Such conditions may range widely in temperature and pH, depending upon the various protecting group manipulations required during construction of specific sequence oligonucleotide. Furthermore, in order to have a sustained therapeutic effect, the analog must be hydrolytically stable to conditions inside the cell. These conditions include not merely an aqueous environment at physiological temperature, but also the presence of large numbers of native hydrolytic enzymes, whose function is to break down polynucleotide and polypeptide macromolecules.

An uncharged oligonucleotide analog is expected to exhibit an increased ability to permeate the hydrophobic cell membrane. Such behavior would be in contrast to polyanionic natural oligonucleotides which are only slowly taken up by cells. An uncharged oligonucleotide should be able to enter the cell by passive diffusion across the lipid membrane, with no dependence on external transport mechanisms. Another potential advantage of uncharged character is increased binding strength in the duplex, since the effect of charge-charge repulsion between the strands is reduced. For example, the methylphosphonate and carboxymethyl analogs exhibit base-pairing interactions with complementary polynucleotides even at low ionic strength, when normal DNA-DNA duplexes are denatured. The contribution of this favorable effect in vivo is uncertain since the presence of the charge-masking effects of solvent and counter-ions must also be considered.

It must also be recognized that the lipophiticity of an analog will play a large role in its solubility and partitioning behavior in the target system. An analog compound cannot be excessively hydrophobic, or questions of aggregation and localization in the membrane may become important. To be most effective the oligonucleotides must be freely soluble in the aqueous environment of the cytoplasm and nucleus.

The antisense strategy invokes the specific interaction of the therapeutic agent with a highly stereoregular target, namely poly-β-D-ribonucleotides. An oligonucleotide analog must be stereochemically compatible with the correct geometry for basepairing. Furthermore, optimization of the base-pairing interaction will probably require that this stereochemistry be consistent throughout the analog structure. This requirement is not easily met for a number of reported analog compounds, such as the phosphorothioates and the methylphosphonates.

In addition to these major design criteria, a number of other considerations come into play in the development of a useful antisense therapeutic: ease of synthesis of specific sequences; amenability to automated synthesis; low toxicity of the compound and metabolites; low cost of large-scale production. These items present significant challenges to the future of antisense drug development.

These important considerations have guided the design of the amide linked oligonucleotide having the following formula:

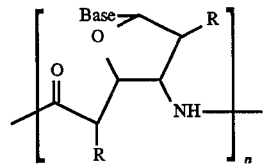

The analog sequence comprises at least two nucleotides. Depending on the desired use of the analog, the synthetic oligonucleotide can be produced with with n up to 1000. Preferably, n is from 2 to 200. More preferably, n is from 2 to 20. Typically, for antisense therapy, the length of the oligonucleotide is only required to be up to approximately 11–15 to define unambiguously a specific target sequence.

Preferably, R is a hydroxyl group, because the 2'- and 5'-hydroxyls enhance water solubility. However, R can be any group that modifies the solubility or binding properties of the analog. Such other groups can be, but are not limited to, hydrogen, or hydrophilic or hydrophobic groups. Hydrophobic groups can be, but are not limited to, aliphatic groups, such as, but not limited to methyl through decyl, or aromatic groups, such as, but not limited to, benzyl. Hydrophilic groups can be, but are not limited to, anionic groups such as carboxylic acids or sulphonic acids, where C is equal to or less than 10, or cationic groups such as, but not limited to, amines or ammonium ions, such as, but not limited to trimethylammonium, or amidines, such as, but not limited to acetamidine, or guanidines, such as, but not limited to methylguanidine. Such other groups can be joined to the nucleic acid analog by means of an ether linkage to either or both of the 3' and 5'oxygens."

Base can be any of the nucleic bases; i.e., uracil, adenine, guanine, cytosine, thymine or hypoxanthine. In the analog, Bases may be the same or different, depending on the sequence of the complementary target gene.

Depending on the desired use, the analog can be produced as described in detail below where the 3'-terminal unit can have a free 3'-amine or, alternatively, be blocked, for example as the azide. Further, the analog can be produced either where the 5'-terminal unit has a free carboxyl, or the 5'-terminal can be blocked, for example, as the carboxamide.

The analog has a stereoregular structure in which non-ionic amide linkages replace the phosphodiester groups of the corresponding naturally-occurring nucleic acid. Further, the analog linkage is conformationally restricted to a significant degree due to the planar geometry and barrier to rotation about the amide bond.

The alkylcarboxamide linkage, in analogy to peptide bonds, is expected to have good chemical stability under the conditions of oligomer synthesis as well as in the cell. Furthermore, since the geometry and reactivity of the planar amide functionality differ markedly from that of the tetrahedral phosphodiester group, the analog linkage should be highly resistant to the action of nucleases. Reactions of phosphate with nucleic-acid binding enzymes typically occur via stabilization of a trigonal bipyramidal phosphorus intermediate. Reaction at the amide carbonyl would instead involve a tetrahedral intermediate, which is not expected to be accommodated by an active enzyme site evolved for phosphate chemistry. Similarly, there is little reason to expect the analog linkage to be susceptible to the action of proteolytic enzymes, in view of the highly dissimilar structure of the amide bond between γ-amino acid nucleoside residues, compared to poly-α-amino acids.

There are several arguments for preparing the analog oligonucleotide in the ribo- vs. the deoxyribo- series. It is generally accepted that the binding strength for oligonucleotide-polynucleotide complexes is strongest for RNA-RNA duplexes and weakest for DNA-DNA duplexes, with RNA-DNA hybrids having intermediate binding strength (Zon, Pharm. Res., 5: 539–549 (1988), which is hereby incorporated by reference). An oligoribonucleoside analog may be able to exploit this binding advantage. Furthermore, the solubility of the oligomeric material in aqueous solution should be enhanced by the presence of hydroxyl groups at both C-2' and C-5'. Finally, synthesis of the monomeric nucleoside analog with the natural configuration of the nucleobase at the anomeric C-1 is facilitated by the presence of the neighboring 2'-hydroxyl.

Physical and computational conformational modeling indicate that the analog should form a duplex with the complementary natural oligonucleotide.

The analog may be used in an antisense treatment method. Antisense therapy involves introducing into a cell a synthetic oligonucleotide (i.e. the analog of the present invention) with a sequence complementary to an mRNA. The analog and the mRNA hybridize, thereby blocking translation of the mRNA into its encoded protein. Specifically, the analog is provided having the formula:

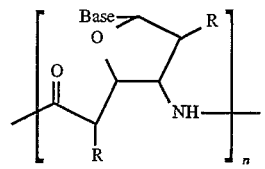

where

R is a hydrogen, a hydroxyl group, a hydrophilic group, or a hydrophobic group, n is greater than or equal to 2, and Base is uracil, adenine, guanine, cytosine, thymine, or hypoxanthine, wherein Bases are the same or different, depending on the sequence of the targeted mRNA. The analog has a sequence complementary to the mRNA. The analog and the mRNA are reacted together to hybridize the analog to the mRNA, whereby translation of the mRNA into its encoded protein is blocked.

The minimum oligonucleotide length theoretically required for specific inhibition of a single mRNA species in human cells was discussed in Haléne, et. al, Oligodeoxynucleotides: Antisense Inhibitors of Gene Expression; CRC Press, Inc.; pp 137–172 (1989)), which is hereby incorporated by reference. On the assumption that only about 0.5% of the $4 \times 10^9$ base pairs of human genomic DNA is transcribed into mRNA, this reference calculates that a mere 11–15 nucleotides are necessary to define unambiguously a specific target sequence. Since A.T occurs more often than G.C in the human genome, the actual minimum length depends on the relative number of A.T vs. G.C base pairs in the target sequence. Consideration of the non-statistical distribution of short nucleotide combinations (n=2, 3, . . . ) should further qualify these limits. In any case, such calculations suggest that even a short sequence of around a dozen nucleotides should be capable of achieving a remarkably high binding specificity.

Another use of the analog involves the field of diagnostics. The analog can serve as a probe which binds to a complementary sequence in a piece of RNA or DNA. This indicates the presence of that complementary sequence in the sample. More specifically, an analog is provided having the formula:

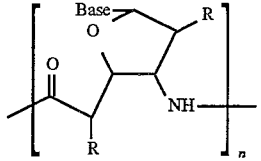

where

R is a hydrogen, a hydroxyl group, an hydrophilic group, or a hydrophobic group, n is greater than or equal to 2, and Base is uracil, adenine, guanine, cytosine, thymine, or hypoxanthine, where the Bases are the same or different, depending on the sequence of the targeted RNA or DNA. The analog is provided with a label, which may be a colored, fluorescent, chemiluminescent, radioactive, or enzymatic material conjugated to the analog. A sample potentially containing a target DNA molecule or a target RNA molecules having a nucleic acid sequence complementary to that of said analog is also provided. The analog and the sample are contacted so that any DNA molecules or any RNA molecules in the sample which are complementary to the analog are hybridized to the analog. Thus, any target DNA molecule or target RNA molecule present in the sample is detected.

with azide at from 70° to 80° C. for 8 to 12 hours at about atmospheric pressure under conditions effective to yield the azido sugar (3).

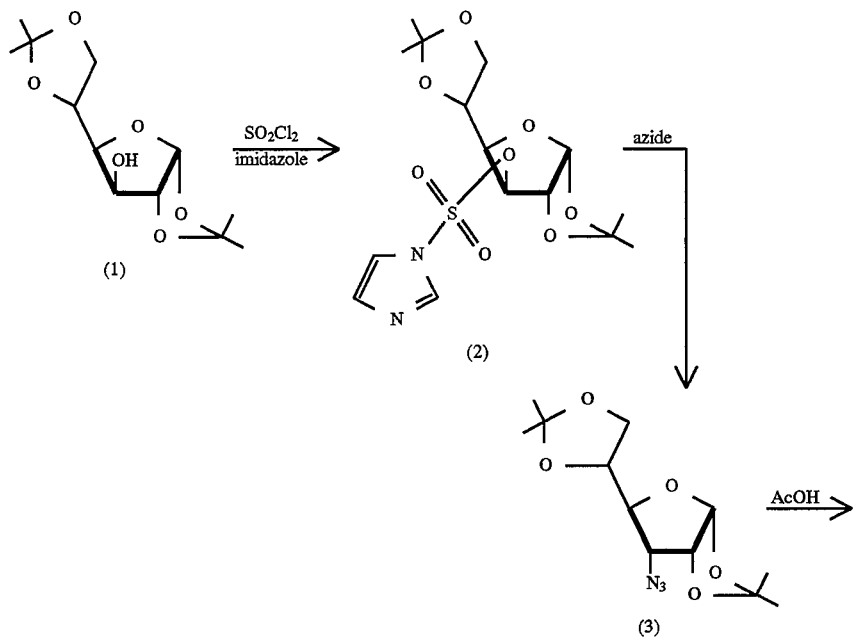

For maximum efficiency as a diagnostic aid, the binding between complementary sequence should be strong. Further, there should also be high discriminations against mismatches, or false positives could result. Due to the three atom internucleotide linkage of the present invention, and the rigid geometry resulting from the linkage, the analog should show strong binding as well as high discrimination against mismatches.

The analog should also be useful in the field of combinational chemistry and information storage. Formation of the amide internucleotide link involves nucleophilic attack on an activated carboxylic acid derivative by an amine. Since the amine is a better nucleophile than the hydroxyl group of a normal nucleoside, the assembly of specific sequences of the polynucleotide analog can be more efficient than assembly of the corresponding sequence of a natural nucleic acid. Thus, the generation of libraries of sequences of the polynucleotide analog will be facilitated. These libraries can then be scanned to identify those sequences that show a desirable property, such as binding to a specific target molecule or transition-state analog, or behavior as a ribozyme analog. Ease of synthesis also means that information storage by synthesis of a specific sequence, where the information is stored in the form of the sequence of bases along the strand, would be facilitated.

The analog is produced by a ten-step synthesis as shown below. Synthesis of the proposed analog ribonucleoside monomer involves modification of the furanose sugar ring to include 6'-carboxyl and 3'-amine functions. The latter is conveniently introduced in masked form as an azide group. To begin, a commercially available di-acetone-D-glucose (1) is reacted with sulfuryl chloride and imidazole at from −60° to 25° C. for 3 to 8 hours at about atmospheric pressure under conditions effective to convert the C-3 hydroxyl to the imidazolylsulfonyl leaving group to produce the imidazolylsulfonyl glucose (2). This is followed by $S_N2$ displacement The azido sugar (3) is reacted with acetic acid at from 30° to 50° C. for 6 to 10 hours, at about atmospheric pressure under conditions effective to open the 5,6-acetal, to produce the ring-opened azido sugar (4). Protection of the C-6 primary hydroxyl is achieved by reacting the ring-opened azido sugar (4) with dimethoxyltrityl (DMT) chloride at from 20° to 25° C. for 1 to 2 hours, at about atmospheric pressure to produce the DMTO acetal (5). The DMTO acetal (5) is reacted with levulinic acid and dicyclohexylcarbodiimide (DCC) at from 0° to 25° C. for 3 to 5 hours, at about atmospheric pressure under conditions effective to produce a levulinate ester (6)(where $R_1$ is a levulinate protecting group).

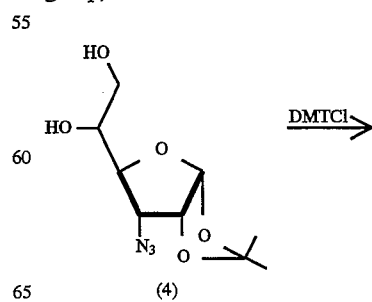

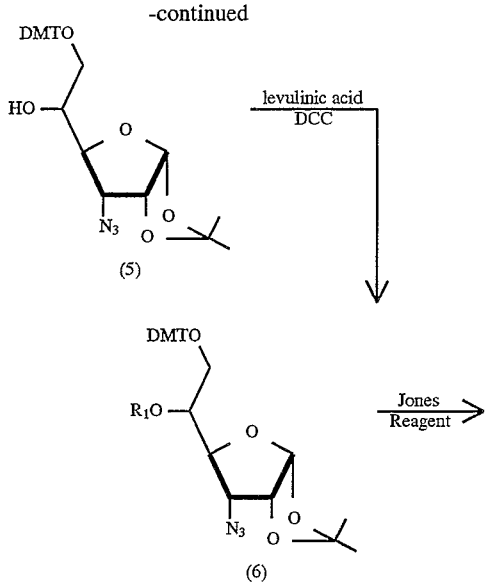

Jones Reagent (chromium oxide, sulfuric acid, and water) is used at from 20° to 25° C. for 1 to 2 hours, under about atmospheric pressure under conditions effective to cleave the DMTO group and to oxidize the resulting primary alcohol to the carboxylic acid (7) acetal. The carboxylic acid acetal (7) is converted to the methyl ester acetal (8) with diazomethane, under conditions effective at from 0° to 5° C. for 20 to 30 minutes, at about atmospheric pressure, followed by opening of the 1,2-acetal with aqueous formic acid at from 50° to 60° C. for 1 to 3 hours under conditions effective to produce the 1-hydroxy compound (9). After acetylation at from 0° to 25° C. for 1–3 hours under conditions effective to yield the 1-acetate ester (10)(with $R_2$ being an acetate protecting group), Base is added to the sugar unit using a Vorbrüggen type glycosidation reaction at from 80° to 85° C. for 1 to 24 hours, which takes advantage of the directing effect of the 2'-acetate to produce exclusively the fully protected monomer (11). Any of the nucleic bases can be added at this point in the synthesis to make the fully protected monomer units for all six nucleic bases. To produce the monomer, the 2'- and 5'hydroxyl protecting groups (i.e. $R_1$ and $R_2$) are removed using methoxide in methanol, at from 20° to 25° C. for 2 to 3 hours, at about atmospheric pressure under conditions effective to produce the alpha hydroxy methyl ester (12).

In some instances it may be desirable to replace the 2'- and 5'-hydroxyl groups with other groups which modify the solubility or binding properties of the analog. It would be apparent to those skilled in the art the procedure to replace the hydroxyl groups with such other groups, which can be, but are not limited to, hydrogen, or hydrophilic or hydrophobic groups. Hydrophobic groups can be, but are not limited to, aliphatic groups, such as, but not limited to methyl through decyl, or aromatic groups, such as, but not limited to, benzyl. Hydrophilic groups can be, but are not limited to, anionic groups such as carboxylic acids or sulphonic acids, where C is equal to or less than 10, or cationic groups such as, but not limited to, amines or ammonium ions, such as, but not limited to trimethylammonium, or amidines, such as, but not limited to acetamidine, or guanidines, such as, but not limited to methylguanidine. Such other groups can be joined to the nucleic acid analog by means of an ether linkage to either or both of the 3' and 5'oxygens.

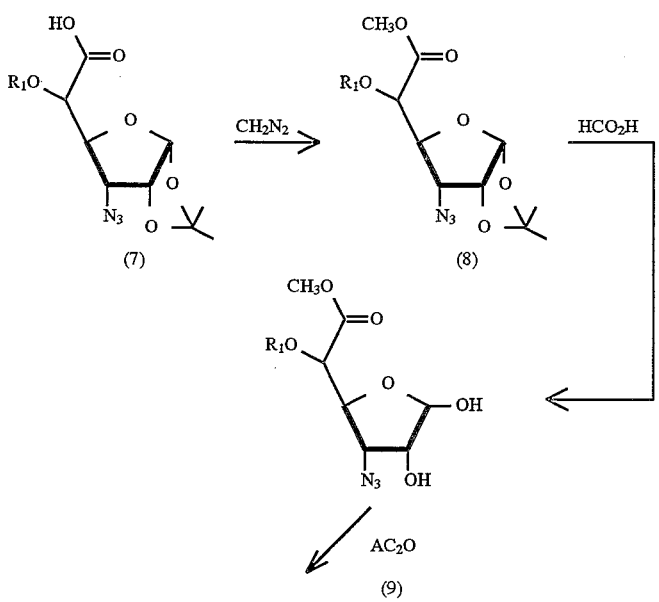

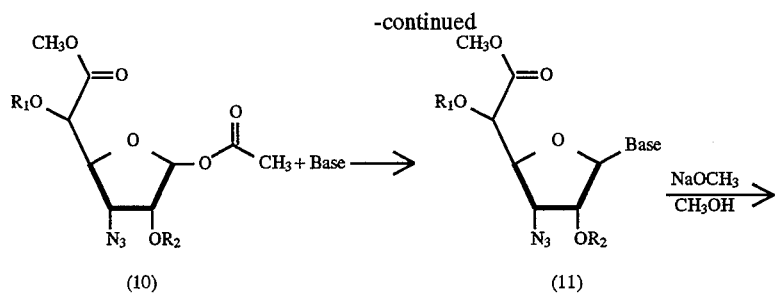

The alpha hydroxy methyl ester (12) is converted to an acid (13) by base hydrolysis at from 20° to 25° for 40 to 80 minutes, under about atmospheric pressure followed by reacting the acid with excess pentafluorophenol and a coupling reagent such as, but not limited to DCC, at from 20° to 25° for 2 to 4 hours under conditions effective to produce the pentafluorophenyl ester (15). Alternatively, the alpha hydroxy methyl ester (12) is reduced using hydrogen gas in the presense of a palladium catalyst at from 20° to 25° for 3 to 5 hours, under about atmospheric pressure under conditions effective to produce the amine (14). Catalyst is removed by filtration. To make a dimer (16), the amine (14) is coupled to the pentafluorophenyl ester (15) in the presense of triethylamine under conditions effective at from 20° to 25° for 2 to 10 minutes, under about atmospheric pressure.

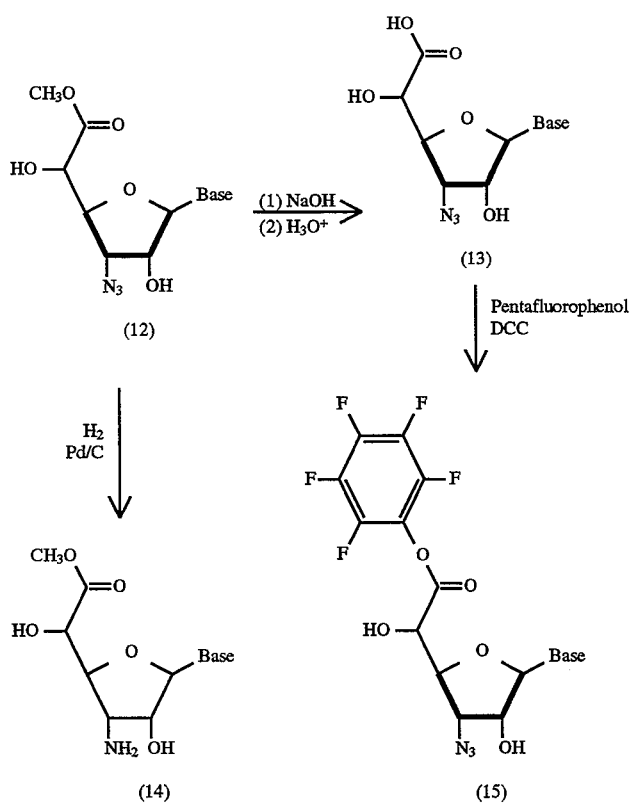

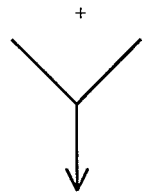

-continued

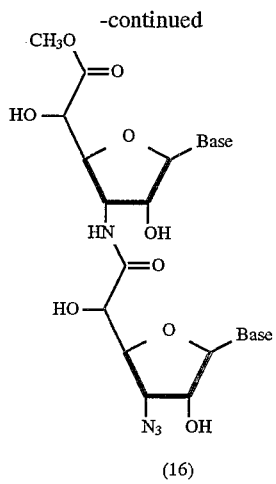

(16)

A nucleic acid analog having the formula:

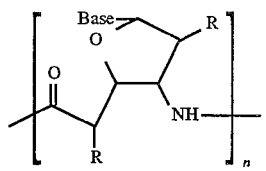

where

R is a compound selected from a group consisting of hydrogen, a hydroxyl group, a hydrophilic group, or a hydrophobic group;

n is greater than or equal to 2; and

Base is uracil, adenine, guanine, cytosine, thymine or hypoxanthine, with Bases in said analog being the same or different, can then be synthesized using the dimer (16). The dimer (16) is repeatedly reacted with additional amines each having the formula:

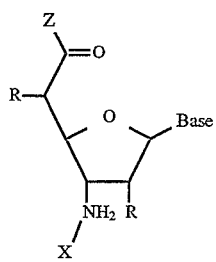

where

Z is a leaving group known to those skilled in the art. Such leaving groups may be, for example, but not limited to, activated esters. Preferably, the leaving group is a pentafluorophenyl ester.

X is any protecting group known to those skilled in the art, such as, for example, but not limited to tert-butyloxycarbonyl (t-BOC).

R is a hydrogen, a hydroxyl group, a hydrophilic group, or a hydrophobic group.

The dimer and each additions amines are reacted together under conditions effective to grow the nucleic acid analog chain. Specifically, the 5'-terminal unit methyl ester is removed by any method known to those skilled in the art. Preferably, base hydrolysis is used to produce the resulting carboxylate. More preferably, the methyl ester is hydrolyzed with 0.2M aqueous sodium hydroxide at 20° to 25° C. for 30 to 90 minutes. Protecting group, X, can be removed from the 3' amine by any method known to those skilled in the art. Preferably, the t-BOC is removed by treatment with anhydrous trifluoro-acetic acid at 20° to 25° C. for 1 to 2 hours. The pH is raised by the addition of, for example, but not limited to diisopropylethylamine, to deprotenate the 3' terminal ammonium cation and make it nucleophilic. Amide bond formation proceeds at 20° to 25° C. for 2 to 10 minutes. As a result, the additional amides are joined to the dimer to produce the nucleic acid analog.

The specific sequence nucleic acid analog can be made by solution phase methods as detailed above. More conveniently, the nucleic acid analog can be produced by synthesis on a solid support. The solid support may be, for example, a controlled pore glass (CPG), a functionalized polystyrene such as a Merrifield resin that has benzylic chloride groups attached to a polystyrene matrix, or an addressable glass or silica wafer.

The nucleic acid analog having the formula:

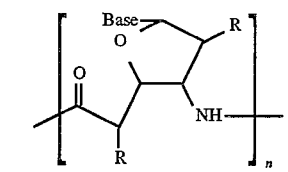

where

R is a compound selected from a group consisting of hydrogen, a hydroxyl group, a hydrophilic group or a hydrophobic group;

n is greater than or equal to 2; and

Base is uracil, adenine, guanine, cytosine, thymine or hypoxanthine, with Bases in said analog being the same or different can be produced by first providing the methyl ester (14). In some instances, it may be desirable to replace the 2'- and 5'-hyroxyl groups with other groups which modify the solubility or binding properties of the analog. It would be apparent to those skilled in the art the procedure to replace the hydroxyl groups such other groups as, but not limited to hydrogen, hydrophilic or hydrophobic groups as discussed above. The methyl ester (14) is treated with di-tert-butyl dicarbonate in dilute aqueous sodium hydroxide, at from 20° C. to 25° C. for from 10 to 30 minutes, under conditions effective to protect the amine as the BOC derivative. The 5'-terminal methyl ester can be removed by any method known to those skilled in the art. Preferably, base hydrolysis is used. More preferably, the methyl ester is hydrolyzed with 0.2M aqueous sodium hydroxide, at from 20° C. to 25° C. for from 30 to 90 minutes. By displacing the chloride from the benzylic chloride of Merrified resin at 60° to 80° C. for 12 to 24 hours, the resulting carboxylate attaches to the solid support as an ester having the formula:

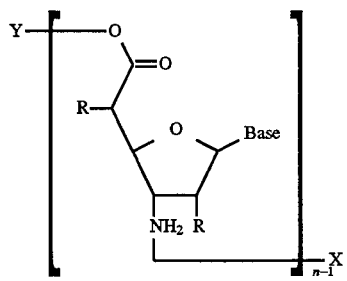

where

R is a hydrogen, a hydroxyl group, a hydrophilic group or a hydrophobic group;

X is any protecting group known to those skilled in the art, such as, for example, but not limited to tert-butyloxycarbonyl (t-BOC). protecting group;

Y is a solid support, such as (CPG), a functionalized polystyrene such as a Merrifield resin that has benzylic chloride groups attached to a polystyrene matrix, or an addressable glass or silica wafer.

The protecting group, X, is removed from the 3'amine by any method known to those skilled in the art. Preferably, X is removed by treatment with anhydrous trifluoroacetic acid at 20° to 25° C. for 1 to 2 hours. The pH is raised by the addition of, for example, but not limited to diisopropylethylamine, to deprotect the 3'-terminal ammonium cation and make it nucleophilic.

Additional amines are then introduced, each having the formula

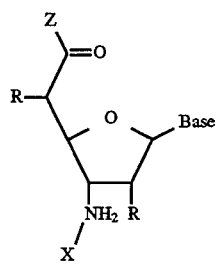

where

Z is a leaving group known to those skilled in the art. Such leaving groups may be, for example, but not limited to, activated esters. Preferably, the leaving group is a pentafluorophenyl ester.

X is any protecting group known to those skilled in the art, such as, for example, but not limited to tert-butyloxycarbonyl (t-BOC).

R is a hydrogen, a hydroxyl group, a hydrophilic group or a hydrophobic group.

The additional amines and the amine intermediate are reacted together at 20° to 25° C. for 2 to 10 minutes under conditions effective to produce a nucleic acid analog. Specifically, the amine intermediate and the additional amines join in a 3'-NH—CO—R-5' linkage. Additional amines can be added repeatedly, the X protecting groups are removed from the end of the growing chain as described above, on the additional amines and the amine intermediate are reacted together until the nucleic acid analog chain is fully formed. The completed chain is removed from the solid support, for example, by treatment with 0.2M aqueous sodium hydroxide at 20° to 25° C. for 1 to 2 hours.

The nucleic acid analogs synthesized by either method discussed above can be inserted into a oligomer having standard phosphodiester linkages.

EXAMPLES

Materials and Methods

Chemicals

The following chemicals were supplied by Aldrich Chemical Co. (Milwaukee, Wis.): imidazole, sulfuryl chloride, sodium azide, diacetone-D-glucose, tetrabutylammonium chloride hydrate, 4,4'-dimethoxytrityl chloride, 4-(N,N-dimethylamino)pyridine, 10% platinum on activated carbon, Diazaid®, hexamethyldisilazane, trimethylsilyl chloride, tin (IV) chloride, and triphenylphosphine. Benzoyladenine and dicyclohexylcarbondiimide were obtained from Sigma (St. Louis, Mo.). Levulinic acid from Eastman Chemical (Kingsport, Tenn.) was purified before use by vacuum distillation (b.p. 95–98, 0.2 mmHg). Acetic anhydride, chromium trioxide, sodium bisulfite, potassium hydroxide, and formic acid were supplied by Mallinckrodt (St. Louis, Mo.).

Pyridine was distilled from calcium hydride and stored over potassium hydroxide pellets. Dimethylformamide was distilled over barium oxide under reduced pressure. Toluene was distilled over calcium hydride. Tetrahydrofuran was distilled from over the sodium ketal of benzophenone.

Spectroscopy $^1$H-NMR spectra were recorded on a Varian XL-200 spectrometer. $^{13}$C-NMR spectra were obtained on a Varian VXR-400 instrument. All δ shift values are reported relative to tetramethylsilane. Optical rotations were measured on a Perkin-Elmer Model 241 Polarimeter. Infrared spectra were recorded on a Mattson Instruments Galaxy Series FT-IR. Mass spectra were obtained on a VG ZAB-SE by the Mass Spectrometry Laboratory, U. Illinois.

Chromatography

Thin-layer chromatography was performed on Merck precoated silica gel 60 $F_{254}$ plates. Flash chromatography was performed on silica gel 32–63 supplied by ICN Biomedicals, using reagent grade solvents. High-performance liquid chromatography was performed on a Waters 5μ NOVA-PAK $C_{18}$ cartridge column in a Waters RCM compression module.

Example 1

3-O-(N-imidazolylsulfonyl)-1,2:5,6-di-O-isopropylidene-α-D-glucofuranose

Diacetone-D-glucose (4.090 g, 15.7 mmol) was dissolved in dimethy formamide (DMF) (50 mL), and the solution cooled in a dry ice/acetone bath. Sulfuryl chloride (2.6 mL, 32.4 mmol, 2 equiv) was added to the cold stirred solution via syringe in portions over 15 minutes. The yellow solution was allowed to warm somewhat over 15 minutes. The cooling bath was then reapplied and imidazole (9.845 g, 152 mmol, 9.7 equiv) was added. The resulting slushy mixture was allowed to warm to room temperature, during which time the solid material melted, giving a yellowish-brown solution. After 4 hours, the somewhat darkened solution was partitioned between chloroform (25 mL) and water (50 mL). The upper aqueous layer was extracted with chloroform (2×25 mL). The combined organic layers were washed with water (3×75 mL), dried over sodium sulfate, filtered, and concentrated under reduced pressure to a colorless syrup. Under vacuum the product slowly crystallized to an off-white solid (5.869 g, 96%).

$^1$H-NMR (CDCl$_3$) δ: 7.97 (dd,1H, J$_{2',5}$=1 Hz, H2'); 7.36 (dd, 1H, J$_{4',5}$=2 Hz, H4'); 7.13 (dd, 1H, H5'); 5.95 (d, 1H, J$_{1,2}$=4 Hz, H1); 4.86 (d, 1H, J$_{3,4}$=1 Hz, H3); 4.73 (d, 1H, H2); 3.9–4.1 (m, 1H, H4), 1.49 (s, 3H, $^i$Pr); 1.32 (s, 3H, $^i$Pr); 1.25 (s, 3H, $^i$Pr); 1.21 (s, 3H, $^i$Pr).

Example 2

3-azido-3-deoxy-1,2:5,6-di-O-isopropylidene-α-D-allofuranose

The imidazylate (1.904 g, 4.877 mmol) and tetra-n-butylammonium chloride hydrate (4.102 g, nominal 14.5 mmol, 3 equiv) were suspended in toluene (27 mL). Sodium azide (969 mg, 14.8 mmol, 3 equiv) was added and the biphasic mixture was heated in an oil bath at 75° C. with stirring overnight. TLC analysis (75:25 petroleum ether/acetone, visualized by charring with H$_2$SO4/heat) of the upper layer of the reaction mixture showed conversion of the starting material Rf0.44 (black spot) to two products, Rf0.56 (red-brown spot) and 0.64 (black-brown spot). The mixture was allowed to cool to room termperature, transferred to a separatory funnel, and washed with water (4×25 mL) and brine (25 mL). The toluene solution was dried over sodium sulfate, filtered, and concentrated under reduced pressure to a colorless syrup. The crude product mixture was separated by flash chromatography (92.5:7.5 petroleum ether/acetone) and the solvent evaporated under reduced pressure to give the faster-eluting olefinic sugar side-product as a fluffy white solid (0.412 g, 35%), followed by the azido sugar as a colorless syrup (0.830 g, 60%).

[α]$^{25}$D=+75° (CHCl$_3$), lit. +72° $^1$H-NMR (CDCL3) δ: 5.78 (d, 1H, J$_{1,2}$=4 Hz, H1); 4.72 (dd, 1H, J$_{2,3}$=5 Hz, H2); 3.95–4.25 (m, 4H, H4, H5, H6, H6'); 3.51 (dd, 1H, J$_{3,4}$=9 Hz, H3); 1.57 (s, 3H, $^i$Pr); 1.48 (s, 3H, $^i$Pr); 1.39 (s, 3H, $^i$Pr); 1.35 (s, 3H, $^i$Pr).

Example 3

3-azido-3-deoxy-1,2-O-isopropylidene-α-D-allofuranose

The azido sugar (0.812 g, 2.85 mmol) was dissolved in 50% aqueous acetic acid (15 mL) and the solution heated at 40° C. in an oil bath with stirring overnight. Analysis by TLC (75:25 petroleum ether/acetone, visualized with H$_2$SO$_4$/heat) revealed complete conversion of the starting compound to product Rf 0.15 (brown). The reaction mixture was frozen and lyophilized to yield the 5,6-diol as an off-white amorphous solid (0.681 g, 98%). This material was used in the next step without further purification.

$^1$H-NMR (CDCl$_3$) δ: 5.81 (d, 1H, J$_{1,2}$=4 Hz, H1); 4.76 (dd, 1H, J$_{2,3}$=5 Hz, H2); 4.10 (dd, 1H, J$_{4,5}$=4 Hz, J$_{3,4}$=9 Hz, H4); 4.00 (dt, 1H, J$_{5,6}$=6 Hz, H5); 3.76 (d, 2H, H6, H6'); 3.59 (dd, 1.H, H3), 1.58 (s, 3H, $^i$Pr); 1.37 (s, 3H, $^i$Pr).

Example 4

3-azido-6-O-(4,4'-dimethoxytrityl)-1,2-O-isopropylidene-α-D-allofuranose

The 5,6-diol (0.198 g, 0.81 mmol) and 4,4'-dimethoxytrityl chloride (0.514 g, 1.52 mmol, 1.9 equiv) were purged under a stream of dry nitrogen for several minutes, and then dissolved in pyridine. The yellow solution was stirred at room temperature under nitrogen for 75 minutes, after which time TLC (70:30 petroleum ether/acetone) indicated a product at Rf 0.29, and no starting material remaining. The reaction was cooled in an ice/water bath and quenched with methanol (ca. 10 mL). The yellow-orange solution was concentrated under reduced pressure with gentle warming in a water bath. The sticky orange residue was redissolved in dichloromethane (10 mL) and washed with 5% aqueous sodium bicarbonate (2×10 mL), water (10 mL), and brine (10 mL). The yellow organic solution was dried over sodium sulfate, filtered, and concentrated under reduced pressure to an orange gum. Flash chromatography (20:65:15 dichloromethane/petroleum either/acetone) afforded the tritylated product as a foam (0.372 g, 84%), accompanied by a small amount of an unidentified highly-colored impurity.

$^1$H-NMR (CDCl$_3$) δ: 6.80–7.56 (m, 13H, DMTr); 5.74, (d, 1H, J$_{1,2}$=3 Hz, H1); 4.68 (dd, 1H, J$_{2,3}$=5 Hz, H2); 4.16 (dd, 1H, J$_{3,4}$=9 Hz, J$_{4,5}$=5 Hz, H4); 4.03 (dt, 1H, J$_{5,6}$=6.5 Hz, H5); 3.78 (s, 6H, OMe); 3.56 (dd 1H, H3); 3.29 (m, 2H, H6, H6'); 1.57 (s, 3H, $^i$Pr).

Example 5

3-azido-3-deoxy-6-O-(4,4'-dimethoxytrityl)-1,2-O-isopropylidene-5-O-5-levulinoyl-α-D-allofuranose The tritylated sugar (0.372 g, 0.68 mmol) and dicyclohexyl-carbodiimide (0.198 g, 1.6 mmol, 2.4 equiv) were purged under a stream of dry nitrogen for several minutes, then dissolved in THF (10 mL) with stirring. Levulinic acid (0.402 g, 3.5 mmol, 5.1 equiv) was added to the yellow solution, causing cloudiness to appear after ca. 5 minutes. The suspension was cooled in an ice/water bath and a catalytic amount of 4-(N,N-dimethyl-amino)pyridine (<5 mg) was added. TLC after 4 hours (5% methanol/dichloromethane) indicated a faster product spot, and the absence of starting material. The reaction was quenched with methanol (10 mL) and the yellow suspension concentrated under reduced pressure. The gummy residue was resuspended in 50:50 dichloromethane/petroleum ether (10 mL) and suction filtered on a sintered glass frit (porosity E). The white dicyclohexylurea precipitate was washed with additional solvent (2×5 mL). The yellow filtrate was concentrated under reduced pressure to a yellow oil with a small amount of white DCU precipitate visible. The product was isolated by flash chromatography (20:65:15 dichloromethane/petroleum ether/acetone) as a yellowish foam (0.319 g, 73%).

$^1$H-NMR (CDCl$_3$) δ: 6.80–7.45 (m, 13H, DMTr); 5.69 (d, 1H, H1); 5.33 (dt, 1H, H5); 4.67 (dd, 1H, H2); 4.32 (dd, 1H, H4); 3.78 (s, 6H, OMe); 3.42 (dd, 1H, H3); 3.20–3.35 (m, 2H, H6, H6'); 2.55–2.80 (m, 4H, —CH$_2$CH$_2$—); 1.54 (s, 3H, $^i$Pr); 1.33 (s, 3H, $^i$Pr).

Example 6

5-O-acetyl-3-azido-3-deoxy-6-O-(4,4'-dimethoxytrityl)-1,2-O-isopropylidene-α-D-allofuranose The 5,6-diol (0.612 g, 2.50 mmol) and 4,4'-dimethoxytrityl chloride (1.370 g, 4.04 mmol, 1.6 equiv) were purged under a stream of dry nitrogen for several minutes, and then dissolved in pyridine (12 mL). The yellow solution was stirred at room temperature under nitrogen. Analysis by TLC (70:30 petroleum ether/acetone) showing starting material remaining after 1 hour. Additional DMTrCl (0.865 g, 2.55 mmol, 1.0 equiv) was added over 1 hour, until the reaction was complete by TLC. The reaction mixture was cooled in an ice/water bath, and acetic anhydride (1.9 mL, 20 mmol, 8 equiv) and a catalytic amount of 4-(N,N-dimethylamino)pyridine (<5 mg) was added. The mixture was stirred for an additional 1.5 hours at room temperature. The reaction was cooled in an ice/water bath and quenched with methanol (ca. 15 mL). The yellow-orange solution was concentrated under reduced pressure with gentle warming in a water bath, and the resultant sticky orange oil was evaporated twice with ethanol. The crude product was generally used without further purification. Purification by flash chromatography (0.3:99.7 methanol/dichloromethane) afforded as a foam (0.862 g, 61%), accompanied by an unidentified highly-colored impurity.

Example 7

3-azido-3-deoxy-1,2-O-isopropylidene-5-O-levulinoyl-α-D-allofuranuronic acid

The protected sugar (0.471 g, 0.73 mmol) was dissolved in acetone (10 mL) and 2.5M Jones' reagent was added dropwise to the yellow stirred solution over 30 minutes (about 1 mL total). There was immediate appearance of an orange-brown color and gradual production of a green precipitate. After 1 hour of stirring, excess chromate was consumed with aqueous sodium bisulfite. Water (10 mL) was added to completely dissolve the green salts. The deep green solution was extracted with ethyl acetate (3×20 mL), and the combined organics were dried over sodium sulfate, filtered, and concentrated under reduced pressure to an orange gum. Purification by flash chromatography (3:3:194 acetic acid/methanol/dichloromethane) gave the uronic acid as a yellow gum (0.243 g, 93%).

$^1$H-NMR (DCDl$_3$) δ: 9.7 (br, 1H, OH); 5.78 (d 1H, $J_{1,2}$=3.5 Hz, H1); 5.39 (d, 1H, $J_{4,5}$=2 Hz, H5); 4.74 (dd, 1H, $J_{2,3}$=4 Hz, H2); 4.43 (dd, 1H, $J_{3,4}$–10 Hz, H4); 3.75 (dd, 1H, H3); 2.65–2.85 (m, 4H, —CH$_2$CH$_2$—); 2.16 (s, 3H, CH$_3$); 1.54 (s, 3H, $^i$Pr); 1.33 (s, 3H, $^i$Pr).

Example 8

5-O-acetyl-3-azido-3-deoxy-1,2-O-isopropylidene-α-D-allofuranuronic acid

The acetylated sugar (0.568 g, 2.0 mmol) was oxidized exactly as for the levulinoyl sugar above. Chromatography afforded the ketone side-product from acyl migration as the first-eluting carbohydrate compound, followed by the desired uronic acid (0.359 g, 60%).

IR: br 3300 cm$^{-1}$ (OH), s 2110 (N$_3$), 1750 (CO). $^1$H-NMR (CDCl$_3$) δ: 10.7 (br, 1H, OH); 5.81 (d 1H, $J_{1,2}$=3 Hz, H1); 5.42 (d, 1H, $J_{4,5}$=2 Hz, H5); 4.76 (dd, 1H, $J_{2,3}$=4 Hz, H2); 4.47 (dd, 1H, $J_{3,4}$=10 Ha, H4); 3.78 (dd, 1H, H3); 2.19 (s, 3H, OAc); 1.59 (s, 3H, $^i$Pr); 1.37 (s, 3H, $^i$Pr).

Example 9 methyl 3-azido-3-deoxy-1,2-O-isopropylidene-5-O-levulinoyl-α-D-allofuranuronate

A diazomethane generation apparatus with clear polished joints was charged with a solution of potassium hydroxide (1.428 g, 25.4 mmol) in 55% aqueous ethanol stirred at 60° C. in an oil bath. A solution of Diazald® (1.170 g, 5.46 mmol) in ether (20 mL) was added dropwise to the base solution, and the diazomethane-containing ethereal vapor was condensed on a cold-finger cooled with dry ice/acetone. The entire apparatus was kept behind a safety shield. The yellow distillate was collected in a flask containing the uronic acid substrate (243 g, 680 mmol), cooled in an ice/water bath. A persistent yellow color in the receiving flask indicated esterification was complete. The excess diazomethane was quenched by dropwise addition of acetic acid, until the yellow color was dispersed. The ethereal solvent was removed under reduced pressure, and the essentially pure product was dried under vacuum to a sticky gum (221 g, 88%).

Example 10 methyl 5-O-acetyl-3-azido-3-deoxy-1,2-O-isopropylidene-α-D-allofuranuronate

The acetyl uronic acid (0.568 g, 2.0 mmol) was esterified in exactly the same manner as for the levulinoyl sugar above, to give the desired uronate ester (0.220 g, 92%).

$[α]^{25}_D$=+142° (CHCL$_3$). $^1$H-NMR (CDCl$_3$) δ: 5.77 (d, 1H, $J_{1,2}$=3 Hz, H1); 5.41 (d, 1H, $J_{4,5}$=3 Hz, H5); 4.74 (dd, 1H, $J_{2,3}$=4 Hz, H2); 4.46 (dd, 1H, $J_{3,4}$=10 Hz, H4); 3.79 (s, 3H, OMe); 3.70 (dd, 1H, H3); 2.17 (s, 3 H. OAc); 1.58 (s, 3H, $^i$Pr); 1.36 (s, 3H, $^i$Pr).

Example 11 methyl 5-O-acetyl-3-azido-3-deoxy-α/β-D-allofuranuronate

The fully protected ester (0.220 g, 0.70 mmol) was dissolved in 70% aqueous formic acid (10 mL) and stirred in an oil bath at 55° C. for two hours. Analysis by TLC (70:30 petroleum ether/acetone) showed complete conversion to a single more polar compound. The reaction mixture was frozen and lyophilized. Residual formic acid was removed by co-evaporation with dichloromethane (2×3 mL). The product, as a yellowish gum, was generally used in the next step without further purification. Chromatography (5:95 methanol/dichloromethane) afforded the pure 1,2-diol (pale yellow gum, 0.143 g, 75%) as an anomeric mixture in a ratio of about 2:3.

$^1$H-NMR (CDCl$_3$) δ: 5.19–5.38 (m, 2 h, H1,5); 4.18–4.48 (m, 3H, H2,3,4); 3.80 (s, 3H, OMe); 3.20 (br, 2H, 1,2-OH); 2.16, 2.19 (2 s, 3H, OAc).

Example 12 methyl 1,2,5-tri-O-acetyl-3-azido-3-deoxy-α/β-D-allofuranuronate

The 1,2-diol (0.143 g, 0.52 mmol) was dissolved in pyridine (6 mL) and the yellowish solution was cooled with stirring in an ice/water bath. Acetic anhydride (2 mL, 21 mmol, 40 equiv) and a catalytic amount of DMAP (<5 mg) were added, and the solution allowed to warm to room temperature. Analysis by TLC (70:30 petroleum ether/acetone) showed loss of starting material within 30 minutes, and formation of a less polar compound. The reaction was quenched with methanol (5 mL) while cooling in an ice/water bath. The yellow solution was concentrated under reduced pressure, and the sticky residue purified by flash chromatography (34:54:12 dichloromethane/petroleum ether/acetone) to give the per-acylated product as an anomeric mixture (colorless plates, 0.168 g, 90%).

$[α]^{25}_D$=+3.4° (CHCl$_3$) $^1$H-NMR (CDCl$_3$) δ: 6.40, 6.54 (d, s, 1H, H1); 5.14–5.36 (m, 1H, H5); 4.29–4.53 (m, 2H, H2,3); 3.83 (s, 1H, H4); 3.78–3.81 (2 s, 3H, OMe); 2.05–2.20 (4 s, 9H, OAc).

Example 13 methyl 1,2-di-O-acetyl-3-azido-3-deoxy-5-O-levutinoyl-α/β-D-allofuranuronate

The levulinoyl methyl ester (0.568 g, 2.0 mmol) was treated with aqueous formic acid and acylated with acetic anhydride, as with the acetyl compound above, giving the per-acylated product (0.220 g, 92%) as a mixture of anomers in about a 1:4 ratio.

$^1$H-NMR (CDCl$_3$) δ: 6.42, 6.18 (d, s, 1H, H1); 5.17–5.49 (m, 2H, H2,5); 4.30–4.55 (m, 2H, H3,4); 3.80 (s, 3H, OMe); 2.65–2.95 (m, 4H, —CH$_2$CH$_2$—); 2.06–2.20 (4 s, 6 H, OAc).

Example 14 methyl 2',5'-di-O-acetyl-3'-azido-1'-(N$^6$-benzoyladenin-9-yl)-3'-deoxy-β-D-allofuranuronate Benzoyladenine (0.166 g, 0.69 mmol) was suspended in 1,2-dichloroethane (3 mL) in the presence of a small mount of activated 3Å molecular sieves. Hexamethyldisilazane (440 uL, 2.0 mmol, 2.9 equiv) and trimethylsilyl chloride (26 uL, 0.20 mmol, 0.29 equiv) were added by syringe. The reaction vessel was fitted with a water-cooled condenser, and the mixture heated at reflux with stirring under nitrogen atmosphere. The suspension became clear within 10 minutes. After 45 minutes at reflux the yellowish solution was allowed to cool. Solvent and excess silylating reagents were evaporated under careful application of aspirator pressure and gentle warming of the reaction vessel leaving the bis(silyl)adenine as a faintly yellow foam.

A solution of the per-acetylated sugar (0.190 g, 0.53 umol) in dichloroethane (0.5 mL) was added to the silylated base and diluted with additional dichloroethane (2.5 mL). Tin (IV) chloride was added as a 1.0M solution in dichloromethane (0.80 uL, 0.80 mmol, 1.5 equiv), causing immediate formation of a white fog and cloudy orange color in the reaction mixture. Heating at reflux was continued for 1.5 hours. The mixture was then allowed to cool, and the reaction neutralized with several drops of concentrated aqueous sodium hydroxide. The mixture was stirred for 30 minutes. The suspension was suction filtered through Celite over glass wool and the filtrate concentrated under reduced pressure to a beige foam. Chromatography (1.5:98.5 methanol/dichloromethane) afforded the protected nucleoside as a pale foam (0.145 g, 51%), $[α]^{25}_D$=−4.5° (CHCL$_3$). FAB-MS: m/z [MH+]539.2; calc. C$_{23}$H$_{22}$N$_8$O$_8$ 538.49 $^1$H-NMR (CDCl$_3$) δ: 8.93 (br, 1H, NH); 8.82 (s, 1H, H8); 8.08 (s, 1H, H2); 7.50–8.05 (m, 5H, aryl); 6.11 (d, 1H, J$_{1',2'}$=4 Hz, H1'); 6.07 (d, 1H, j$_{2',3'}$=6 Hz, H2'); 5.43 (d, 1H, J$_{4',5'}$=3 Hz, H5'); 5.00 (dd, 1H, J$_{3',4'}$=7 Hz, H3'); 4.48 (dd, 1H, J$_{3',4'}$=7 Hz, H3'); 4.48 (dd, 1H, H4'); 3.78 (s, 3H, OMe); 2.20 (s, 3H, OAc); 2.10 (s, 3H, OAc).

Example 15 methyl 2'-O-acetyl-3'-azido-1'-(N$^6$-benzoyladenin-9-yl)-3'-deoxy-5'-O-levulinoyl-β-D-allofuranuronate The pre-acylated levulinoyl sugar was condensed with benzoyladenine as for the tri-acetyl derivative above, to give the nucleoside (85 mg, 58%) following purification by several cycles of flash chromatography.

$^1$H-NMR (CDCl$_3$) δ: 9.18 (br, 1H, NH); 8.80 (s, 1H, H8); 8.23 (s, 1H, H2); 7.50–8.00 (m, 5H, aryl); 6.16 (d, 1H, J$_{1',2'}$=4 Hz, H1); 6.04 (dd, 1H, J$_{2',3'}$=6, H2'; 5.44 (d, 1H, J$_{4',5'}$=3 Hz, H5'); 4.93 (dd, 1H, J$_{3',4'}$=6 Hz, H3'); 4.49 (dd, 1H, H4'); 3.77 (s, 3H, OMe); 2.50–2.80 (m, 4H, —CH$_2$CH$_2$—); 2.18 (s, 3H, OAc); 2.15 (s, 3H, OAc).

Example 16 methyl 2',5'-di-O-acetyl-3'-amino-1'-(N$^6$-benzoyladenin-9-yl)-3'-deoxy-b-D-allofuranuronate To the protected nucleoside (4 mg, 7 umol) in tetrahydrofuran (100 uL) was added triphenylphosphine (5 mg, 19 umol), and the solution was stirred at RT. After 30 minutes, water (5 uL) was added, and the stirring continued for 5 hours, after which time TLC (10:90 methanol/dichloromethane) indicated disappearance of starting material. The solution was concentrated under reduced pressure to a cloudy gum. Flash chromatogrphy (4.5:95.5 methanol/dichloromethane) afforded the aminonucleoside (<4 mg).

FAB-MS: m/z [MH+]513.2; calc. C$_{23}$H$_{24}$N$_6$O$_8$ 512.48 $^1$H-NMR (CDCL$_3$) δ: 8.85 (s, 1H, H8); 814 (s, 1H, H2); 7.40–8.10 (m, 5H, aryl); 6.15 (d, 1H, J$_{1',2'}$=3 Hz, H1'); 5.87 (dd, 1H, J$_{3',3'}$32 9 Hz, H2'); 5.35 (d, 1H, J$_{4',5'}$=4 Hz, H5'); 5.08 (dd, 1H, J$_{3',4'}$=3 Hz, H3'); 4.58 (dd, 1H, H4') 3.72 (s, 3H, OMe); 2.11 (s, 3H, OAc); 2.01 (s, 3H, OAc).

Example 17

3'-azido-1'-(N$^6$-benzoyladenin-9-yl)-3'-deoxy-β-D-allofuranuronic acid

The protected nucleoside (13 mg, 24 umol) was dissolved in 0.5N NaOH (1 mL), giving a bright yellow solution. The color faded over 30 minutes of stirring at room temperature. The solution was then applied to a pipet column of Dowex 50W cation exchange resin (50X4-200, H$^+$ form) that had been prewashed with distilled water (125 mL). The column was eluted with water (25 mL), followed by 20:80 methanol/water (100 mL) and 40:60 methanol/water (100 mL). The product was recovered from lyophilization as a small amount of fluffy white powder (<5 mg).

$^1$H-NMR (DMSO) δ: 11.20 (s, 1H, NH); 8.75 (s, 1H, H8); 8.66 (s, 1H, H2); 7.50–8.10 (m, 5H, aryl); 6.40 (d, 1H, J$_{2',OH}$=6,2'-OH); 6.08 (d, 1H, J$_{1',2'}$=5, H1'); 4.98 (m, 1H, H2'); 4.32 (br, 1H, H5'); 4.29 (br, 2H, H3', 4').

Example 18

3'-azido-1'-(adenin-9-yl)-3'-deoxy-b-D-allofuranuronamide

The protected nucleoside (22 mg, 41 umol) was dissolved in saturated methanolic ammonia (1 mL) and stirred at RT in a sealed test tube overnight, during which time a fine white precipitate appeared. The solvent was removed under reduced pressure. The pale powdery residue was suspended in distilled water (4 mL) and washed with ether (4×2 mL). The aqueous suspension was centrifuged and the supernatant removed by pipet. The pellet was washed with water (4 mL) and dried under vacuum, giving the amido-nucleoside as a beige powder (9 mg, 71%).

$^1$H-NMR (DMSO) δ: 8.32 (s, 1H, H8); 8.15 (s, 1H, H2); 7.50 (br, 4H, 2 NH$_2$); 7.01 (d, 1H, j$_{5',OH}$=4 Hz, 5'-OH); 6.28 (d, 1H, J$_{2',OH}$=5 Hz, H1', H2'); 5.90 (d, 1H, J$_{1',2'}$=6 Hz, H1'); 4.93 (dd, 1H, J$_{2',3'}$=6 Hz, H2'); 4.29 (m, 1H, J$_{3',4'}$2 Hz, H3'); 4.19 (m, 2H, H4', 5').

Example 19

3'-amino-1'-(adenin-9-yl)-3'-deoxy-b-D-allofuranuronamide

To the amido-nucleoside (7 mg, 21 umol) in DMSO (1 mL) was added triphenylphosphine (38 mg, 145 umol), which dissolved with stirring over ten minutes. After three hours, another portion of triphenylphosphine (31 mg, 118 umol) was added. After another 24 hours the reaction was quenched with conc. NH₄OH (2 mL), causing the solution to warm slightly and a whitish precipitate to form. The solution was lyophilized, leaving an amorphous white residue which was washed with dichloromethane (4×1 mL) and dried under vacuum.

¹H-NMR (DMSO) δ: 8.16 (s, 1H, H8); 8.30 (s, 1H, H2); 7.58 (br, 2H, Ad-NH₂); 7.46 (br, 4H, 2NH₂); 6.85 (d, 1H, 5'-OH); 6.60 (br, 1H, 2'-OH); 6.08 (d, 1H, H1'); 4.88 (m, 1H, H2'); 4.40 (br, 1H, H4'); 4.20 (br, 1H, H5'); 3.90 (m, 1H, H3').

Example 20

U$_{NH}$U Dimer

The U$_{NH}$U dimer was produced according to the synthesis as described in the detailed description of the invention. Tests were undertaken to determine evidence of the dimer structure.

Evidence for Dimer Structure

¹H NMR: The H-6 peak of uracil appears as a doublet around 8.0 ppm and is the only peak in this region. The NMR of the dimer in CD₃OD shows two doublets (8.00 ppm, J=8 Hz; 7.77 ppm, J=8 Hz) of equal intensity representing the two H-6 protons from the two different uracil bases. The remainder of the spectrum is more crowded because of overlapping sugar proton signals, but is consistent with the dimer structure.

FAB-Mass Spec: m/z[M+H⁺]597.2; calc. C₂₁H₂₄N₈O₁₃ 596.47

This MS was taken for a compound prepared by direct coupling between the acid and the amine using the benzotriazol-1-yloxytripyrrolidinophosphonium hexafluorophosphate (PyBOP) coupling reagent. All other analytical data given here were generated from the dimer prepared by coupling of the ester with the pentafluorophenyl ester. The dimers derived from the two different pathways had identical HPLC retention times.

TLC: Whereas the amine stained positive for ninhydrin, the dimer was negative for ninhydrin, indicating that it did not contain an amine. This is consistent with an amide-linked dimer but not with an ester-linked dimer.

Hydrolysis studies: NMR and MS data clearly indicated a dimer, but these two techniques would not distinguish between an amide-linked dimer and an ester-linked dimer. Since amines are more reactive than hydroxyls it was assumed that an amide linkage would be formed during the final coupling step, and this is what was indicated by the TLC data just cited. However, to confirm further that an amide had formed, the dimer was subjected to basic conditions which should quickly hydrolyze an ester but would hydrolyze an amide very slowly. Hydrolysis in acid was also done. The dimer was purified by HPLC before each hydrolysis study and the hydrolysis reactions (all run at 25 C) monitored by HPLC.

0.1N NaOH: Controls: The alpha hydroxy methyl ester and the amine monomers both showed complete hydrolysis of the methyl ester after 35 minutes.

Dimer: After 40 minutes, the dimer peak had been completely converted to a new peak consistent with an amide-linked dimer that had lost the methyl ester. After 3 days, approximately 30% hydrolysis to monomer units had occurred.

1.ON NaOH: After 17.75 hr, 5% hydrolysis into monomer units had occurred.

1.ON HCl After 20.75 hr, approximately ⅓ of the dimer had been converted to dimer lacking the methyl ester. A small amount of conversion to monomers may have occurred but interpretation is difficult due to interference in that region of the chromatogram.

Although the invention has been described in detail for the purpose of illustration it is understood that such detail is solely for that purpose and variations can be made therein by those skilled in the art without departing from the spirit and the scope of the invention which is defined by the following claims.

What is claimed:

1. A nucleic acid analog having the formula:

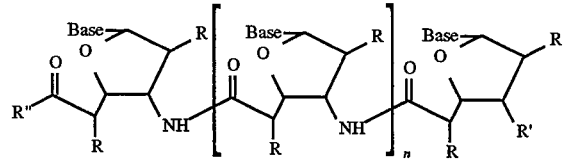

where

R is a compound selected from a group consisting of hydrogen, a hydroxyl group, a hydrophilic group or a hydrophobic group;

R' is a compound selected from a group consisting of an amine group or an azide;

R" is a compound selected from a group consisting of an amine group, a hydroxyl group, or an methoxy group;

n is greater than or equal to 1; and

Base is uracil, adenine, guanine, cytosine, thymine or hypoxanthine, with Bases in said analog being the same or different.

2. A nucleic acid analog according to claim 1, wherein R is a hydroxyl group.

3. A nucleic acid analog according to claim 1, wherein n is from 2 to 1000.

4. A nucleic acid analog according to claim 3, wherein n is from 2 to 200.

5. A nucleic acid analog according to claim 4, wherein n is from 2 to 20.

6. A nucleoside analog having the formula:

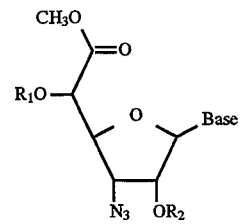

where

R₁ and R₂ are protecting groups;

Base is thymine, adenine, guanine, cytosine, uracil or hypoxanthine.

7. A process for producing a nucleic acid analog comprising:

providing an amine having the formula:

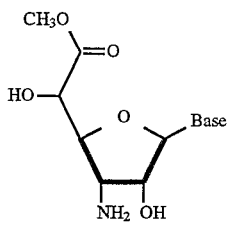

where Base is uracil, adenine, guanine, cytosine, thymine or hypoxanthine;

providing a pentafluorophenyl ester having the formula:

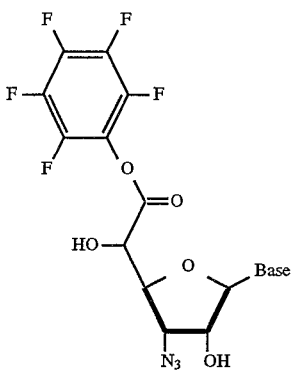

where Base is uracil, adenine, guanine, cytosine, thymine or hypoxanthine; and reacting the amine and the pentafluorophenyl ester under conditions effective to produce a nucleic acid analog having the formula:

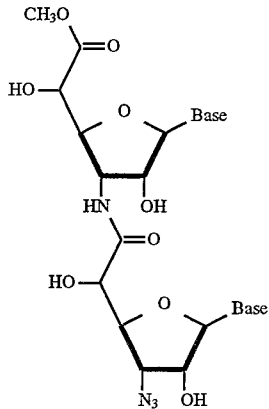

8. A process according to claim 7, which further comprises:

repeatedly reacting said nucleic acid analog with additional amines, each having the formula

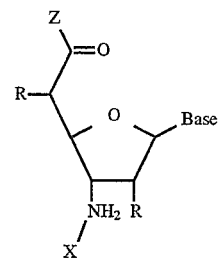

where
Z is a leaving group;
X is a protecting group;
R is a hydrogen, a hydroxyl group, a hydrophilic group, or a hydrophobic group;

under conditions effective to produce a nucleic acid analog having the formula:

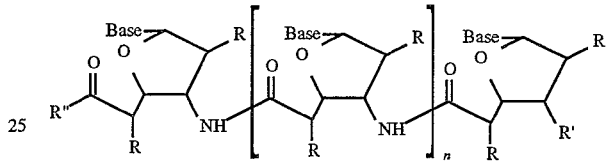

where
R is a compound selected from a group consisting of hydrogen, a hydroxyl group, a hydrophilic group or a hydrophobic group;
R' is a compound selected from a group consisting of an amine group or an azide; and
R" is a compound selected from a group consisting of an amine group, a hydroxyl group, or an methoxy group;
n is greater than or equal to 1; and
Base is uracil, adenine, guanine, cytosine, thymine or hypoxanthine, with Bases in said analog being the same or different.

9. A process according to claim 8, wherein R is a hydroxyl group.

10. A process according to claim 8, wherein n is from 3 to 1000.

11. A process according to claim 10, wherein n is from 3 to 200.

12. A process according to claim 11, wherein n is from 3 to 20.

13. A process according to claim 7, wherein said providing the pentafluorophenyl ester comprises:

providing an alpha hydroxy methyl ester having the formula:

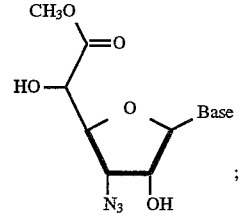

converting a first portion of the alpha hydroxy methyl ester to an acid having the formula:

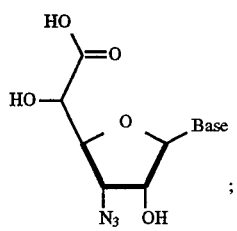

reacting the acid with excess pentafluorophenol under conditions effective to form the pentafluorophenyl ester; and said providing the amine comprises:

reducing a second portion of the alpha hydroxy methyl ester under conditions effective to form the amine.

14. A process according to claim 13, wherein said providing an alpha hydroxy methyl ester comprises:

providing a fully protected monomer having the formula:

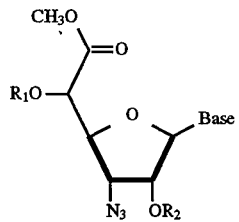

where $R_1$ is a levulinate protecting group $R_2$ is an acetate protecting group; and reacting the monomer with methoxide in methanol under conditions effective to remove levulinic acid and the acetate protecting groups and to produce the alpha hydroxy methyl ester.

15. A process according to claim 14, wherein said providing a fully protected monomer comprises:

providing a 1-acetate ester having the formula:

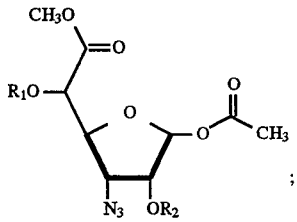

providing Base; and reacting Base and the 1-acetate ester under conditions effective to produce the fully protected monomer.

16. A process according to claim 15, wherein said providing a 1-acetate ester comprises:

providing a 1-hydroxy compound having the formula:

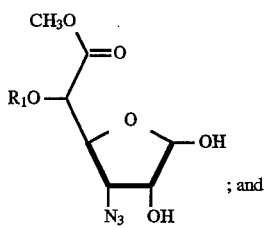

acetylating the 1-hydroxy compound under conditions effective to yield the 1 acetate ester.

17. A process according to claim 16, wherein said providing a 1-hydroxy compound comprises:

providing a methyl ester acetal having the formula:

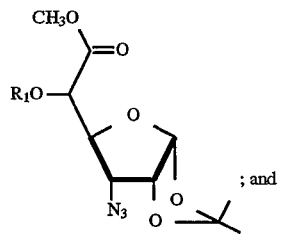

reacting the methyl ester acetal with aqueous formic acid under conditions effective to produce the 1-hydroxy compound.

18. A process according to claim 17, wherein said providing a methyl ester acetal comprises:

providing a carboxylic acid acetal having the formula:

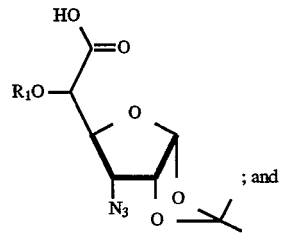

reacting the carboxylic acid acetal with diazomethane under conditions effective to convert the carboxylic acid acetal to the methyl ester acetal.

19. A process according to claim 18, wherein providing the carboxylic acid acetal comprises:

providing a levulinate ester having the formula:

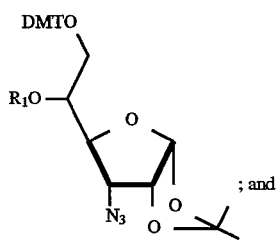

reacting the levulinate ester with Jones Reagent under conditions effective to produce the carboxylic acid acetal.

20. A process according to claim 19, wherein said providing the levulinate ester comprises:

providing a DMTO acetal having the formula:

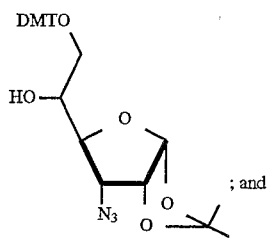
(5)

; and reacting the DMTO acetal with levulinic acid under conditions effective to produce the levulinate ester.

21. A process according to claim 20, wherein said providing a DMTO acetal comprises:

providing a ring-opened azido sugar having the formula:

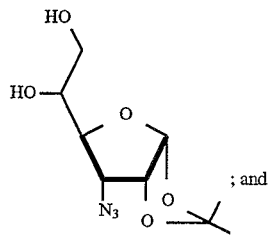
; and reacting the ring-opened azido sugar with dimethoxytrityl chloride under conditions effective to protect the DMTO acetal.

22. A process according to claim 21, wherein said providing a ring-opened azido sugar comprises:

providing an azido sugar having the formula:

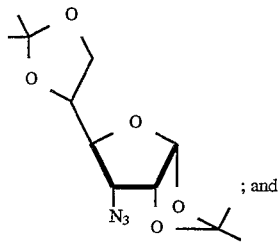
; and reacting the azido sugar with acetic acid under conditions effective to produce the ring-opened azido sugar.

23. A process according to claim 22, wherein said providing an azido sugar comprises:

providing a imidazolylsulfonyl glucose having the formula:

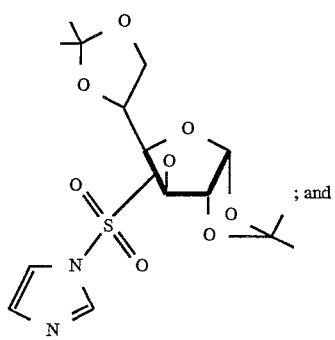
; and reacting the imidazolylsulfonyl glucose with an azide under conditions effective to produce the azido sugar.

24. A process according to claim 23, wherein said providing a imidazolylsulfonyl glucose comprises:

providing a di-acetone-D-glucose having the formula:

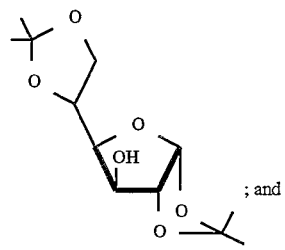
; and reacting the di-acetone-D-glucose with sulfuryl chloride and imidazole under conditions effective to produce the imidazolylsulfonyl glucose.

25. A process for making a nucleic acid analog having the formula:

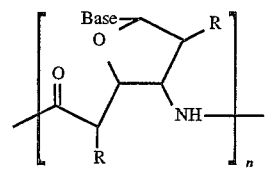

where

R is a compound selected from a group consisting of hydrogen, a hydroxyl group, a hydrophilic group or a hydrophobic group;

n is greater than or equal to 2; and

Base is uracil, adenine, guanine, cytosine, thymine or hypoxanthine, with Bases in said analog being the same or different, said process comprising:

providing an amine intermediate having the formula:

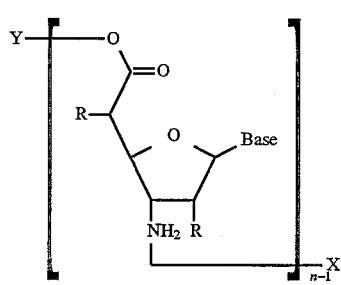

where

R is a compound selected from a group consisting of hydrogen, a hydroxyl group, a hydrophilic group or a hydrophobic group;

X is a protecting group

Y is a solid support;

reacting said mine intermediate with an acid under conditions effective to remove the protecting group and to make said amine intermediate nucleophilic; and reacting the amine intermediate with additional amines, each having the formula:

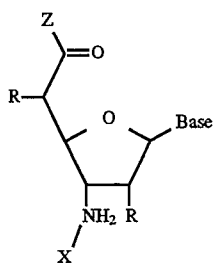

where

Z is a leaving group,

X is a protecting group,

R is a compound selected from a group consisting of hydrogen, a hydroxyl group, a hydrophilic group or a hydrophobic group; under conditions effective to produce the nucleic acid analog.

26. A process according to claim 25 which further comprises:

removing the nucleic acid analog from the solid support.

27. A process according to claim 25, wherein said providing an amine intermediate comprises:

providing a first amine having the formula:

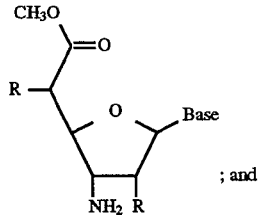; and where

R is a compound selected from a group consisting of hydrogen, a hydroxyl group, a hydrophilic group, or a hydrophobic group; and reducing the first amine under conditions effective to form the amine intermediate.

28. A process according to claim 25, wherein R is a hydroxy group.

29. A process according to claim 25, wherein n is from 2 to 1000.

30. A process according to claim 29, wherein n is from 2 to 200.

31. A process according to claim 30, wherein n is from 2 to 20.

32. A nucleic acid analog having the formula:

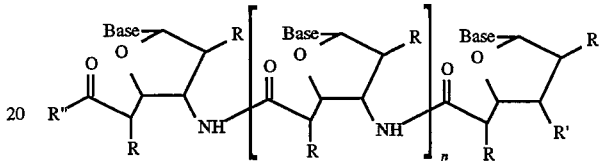

where

R is a compound selected from a group consisting of hydrogen, a hydroxyl group, a hydrophilic group or a hydrophobic group;

R' is a compound selected from a group consisting of an amine group or an azide;

R" is a compound selected from a group consisting of an amine group, a hydroxyl group, or an alkoxy group;

n is greater than or equal to 1; and

Base is uracil, adenine, guanine, cytosine, thymine or hypoxanthine, with Bases in said analog being the same or different.

* * * * *